United States Patent [19]
Raulerson

[11] Patent Number: 5,346,471
[45] Date of Patent: Sep. 13, 1994

[54] DUAL LUMEN CATHETER

[76] Inventor: J. Daniel Raulerson, 1205 Belleville Ave., Brewton, Ala. 36426

[21] Appl. No.: 35,035

[22] Filed: Mar. 22, 1993

[51] Int. Cl.$^5$ ............................................. A61M 3/00
[52] U.S. Cl. ....................................... 604/43; 604/48; 604/284
[58] Field of Search ..................... 604/39, 43, 48, 280, 604/284, 53

[56] References Cited

U.S. PATENT DOCUMENTS

| | | | |
|---|---|---|---|
| 3,633,579 | 1/1972 | Alley et al. | 604/280 |
| 4,493,696 | 1/1985 | Uldall | 604/43 |
| 4,687,471 | 8/1987 | Twardowski et al. | 604/280 |
| 4,838,881 | 6/1989 | Bennett | 604/280 |
| 5,009,636 | 4/1991 | Wortley et al. | 604/280 |
| 5,149,330 | 9/1992 | Brightbill | 604/280 |
| 5,156,592 | 10/1992 | Martin et al. | 604/43 |

FOREIGN PATENT DOCUMENTS 2017499  10/1979  United Kingdom .................. 604/43

*Primary Examiner*—Jerome L. Kruter
*Attorney, Agent, or Firm*—A. W. Fisher, III

[57] ABSTRACT

A coaxial configured dual lumen catheter for hemodialysis treatment and the like comprising an outer extraction lumen having an inner return lumen disposed therein configured to be coupled between a patient and a dialysis device, the outer extraction lumen and the inner return lumen are similarly configured to cooperatively form a proximal section coupled to the dialysis device, an arcuate intermediate section and a distal section to be placed into the patient wherein the cross-sectional area of the outer extraction lumen and inner return lumen in the arcuate section is greater than the cross-sectional area of the outer extraction lumen and the inner return lumen in the distal section to compensate for the increase in friction and turbulence created by the arcuate configuration and thereby more evenly distribute fluid flow pressure through the dual lumen catheter.

5 Claims, 2 Drawing Sheets

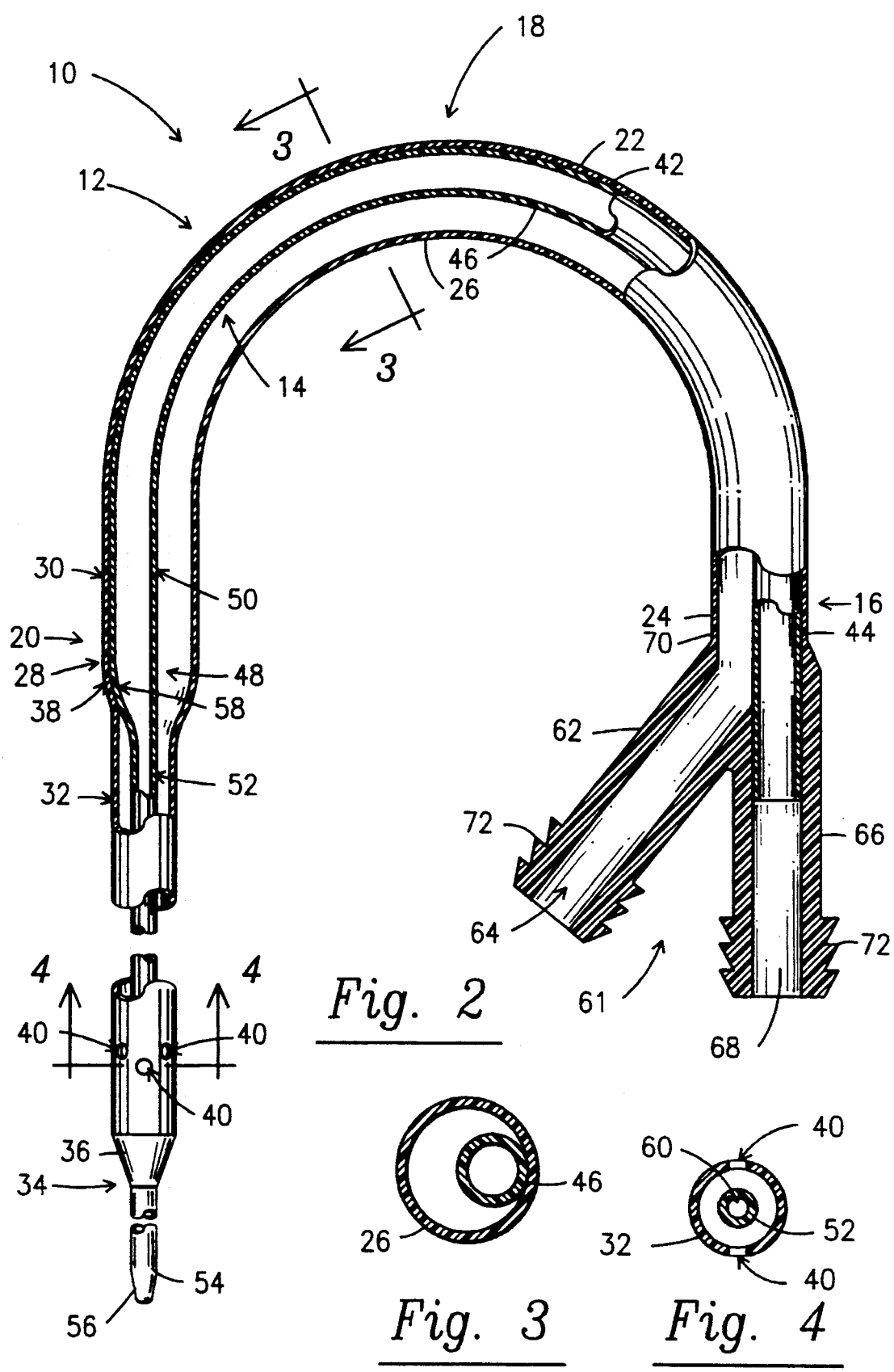

DUAL LUMEN CATHETER

BACKGROUND OF THE INVENTION

1. Field of the Invention

A dual lumen catheter for use in hemodialysis treatment and the like.

2. Description of the Prior Art

Currently, there are three basic catheter configurations available for temporary hemodialysis. They are the coaxial configuration, the side-by-side configuration and the triple-lumen configuration in which a third smaller lumen for placement over a guide wire is located in the partition between the two blood transmission channels. All work well when they are maintained in a straight fashion. If they are bent accidentally or for tape-down purposes, blood flow is restricted, or worse, the catheters will kink and occlude. The invention herein described compensates for the need to curve a catheter by expanding the diameter of the lumens in the bend to neutralize the increased friction and turbulence which is created by the bend. Otherwise this friction and turbulence is translated into resistance to blood flow with increased pressure in the blood flow path. This catheter can be placed in either internal jugular or subclavian veins and still be secured to the relatively flat anterior chest wall. Taping in this location allows the patient to engage in normal activities without the catheter being noticed, becoming kinked or being inadvertantly dislodged.

U.S. Pat. No. 4,961,809 describes a dual lumen catheter for insertion into a vein of a patient for use in hemodialysis treatments having a first and second portion defining a shorter intake lumen and a longer return lumen respectively. The intake lumen is closed at the end and receives blood through at least one opening in the side wall of the catheter; while, the second lumen includes the second portion which is of smaller cross-section than the first portion.

U.S. Pat. No. 5,057,073 shows a dual lumen catheter for insertion into a vein of a patient for use in hemodialysis treatments having first and second portions defining a shorter intake lumen and a longer return lumen substantially identical to U.S. Pat. No. 4,961,809.

U.S. Pat. No. 4,895,561 teaches a dual lumen catheter assembly comprising a lumen 14 gradually changing from a D-shape at the tip 15 to a circular shape.

U.S. Pat. No. 4,692,141 describes a double lumen catheter having an elongated tube with a proximal first cylindrical portion having an internal divider to define a pair of discrete lumens including a shorter lumen opening at the distal end of the first cylindrical portion and a longer lumen opening at the distal end of the elongated tube where the return lumen 13 changes in cross-sectional area.

U.S. Pat. No. 4,990,133 shows a ureteral catheter stent including an elongated, relatively flexible, hollow tubular member having a plurality of drainage openings extending through a wall and having two end portions each being in the form of a hook and having at least one male and/or female interlocking unit formed into the end of at least one hook.

U.S. Pat. No. 4,493,696 teaches a double lumen cannula for hemodialysis comprising elongated flexible tubular members disposed one within the other for semi-permanent insertion into a central vein of a patient. Both members are sufficiently flexible to permit curving on a 12 cm radius without reduction in internal cross-section so as to avoid constriction of fluid flows.

Re. 31,873 describes a venous catheter device including a plurality of independent and noncommunicating fluid conveying lumens housed within or formed in a single catheter.

U.S. Pat. No. 5,053,023 shows a flexible dual lumen catheter for use in prolonged access including an elongated body having side-by-side lumens for receiving body fluid and other being a return lumen for leading fluid to the body.

U.S. Pat. No. 4,961,731 teaches a non-whip angiographic catheter having a preselected number of openings of preselected size, location and orientation along the straight portion of the catheter near the distal tip so as to distribute the force of the high-pressure dye injection jets while maintaining the non-whip characteristic.

U.S. Pat. No. 4,772,268 describes a dual lumen hemodialysis catheter including a tube having a circular external cross section rotatably received within a fitting. The fitting may be attached to the patient by sutures or the like and rotatably mounts the tube of the catheter. Stop means are provided on opposite sides of the fitting preventing the tube of the catheter from moving longitudinally relative to the fitting.

U.S. Pat. No. 4,626,240 shows a dual lumen central vein cannula for use in hemodialysis where the lumens are formed by a septum dividing an essentially circular tube longitudinally. A manifold at the proximal end of the tube separately distributes blood into the return lumen and collects blood from the inlet lumen.

Additional examples of the prior art are shown in U.S. Pat. No. 4,037,599; U.S. Pat. No. 4,134,402; U.S. Pat. No. 4,203,436; U.S. Pat. No. 4,583,968 and U.S. Pat. No. 4,682,978.

SUMMARY OF THE INVENTION

The present invention relates to a dual lumen catheter configured to be operatively coupled between a patient and a dialysis device for hemodialysis treatment or the like comprising an outer extraction lumen having an inner return lumen disposed therein.

The outer extraction lumen comprises a hollow extraction tube or conduit including a proximal extraction portion, an arcuate intermediate extraction portion and a distal extraction portion comprising a first extraction region having a first diameter and a second extraction region having a second diameter less than the first diameter of the first extraction region disposed in operative communication relative to each other by an extraction transition region. A plurality of extraction apertures is formed through the wall of the second extraction region.

The inner return lumen comprises a hollow return tube or conduit including a proximal return portion, an arcuate intermediate return portion and a substantially straight distal return portion comprising a first return region having a first diameter and a second return region having a second diameter less than the first diameter of the first extraction region disposed in operative communications relative to each other by a return transition region. A return aperture is formed in the end of the second return region.

This dual lumen catheter is normally placed in the internal jugular vein of a patient for which it is uniquely suited. Since the internal jugular vein runs parallel to the long axis of the body and is entered at the base of the neck dorsal to the clavicle, straight catheters used in this location have to be secured to the side of the neck and usually end up kinking, whereas the arcuate configuration can be secured to the anterior chest wall and thereby resists kinking. Internal jugular catheterization is becoming the preferred method of temporary dialysis since it is not predisposed to stenosis as is the case with subclavian catheterization. However, the arcuate configuration does not limit its use to the internal jugular. In patients with narrow chests or where entry into the subclavian is more lateral than usual the arcuate configuration will permit it to be secured to the anterior chest wall without risk of kinking. The dual lumen catheter may be secured in place by a conventional dressing and attachment fitting having wing tabs.

For use in hemodialysis, the double lumen catheter is introduced in the direction of blood flow in a large vein. The arcuate design of the double lumen catheter requires a Seldinger's guide wire or placement through a sheath as described in U.S. Pat. No. 5,057,073. The blood is drawn from the patient through a plurality of extraction apertures and outer extraction lumen for processing by the dialysis device and is returned through the inner return lumen and return aperture.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 2 is a cross-sectional side view of the dual lumen catheter.

FIG. 3 is a cross-sectional end view of the dual lumen catheter taken along line 3—3 of FIG. 2.

FIG. 4 is a cross-sectional end view of the dual lumen catheter taken along line 4—4 of FIG. 2.

Similar reference characters refer to similar parts throughout the several views of the drawings.

DETAILED DESCRIPTION OF THE PREFERRED EMBODIMENT

Figure 5:
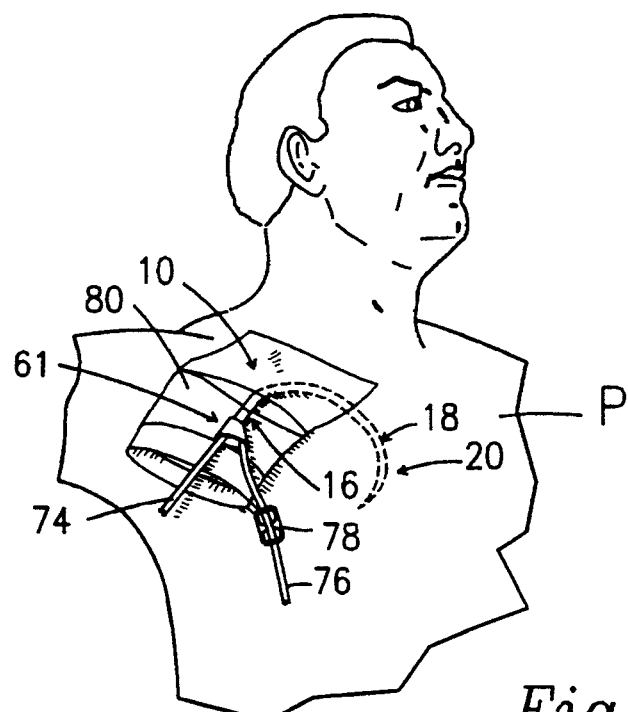
FIG. 5 is a diagrammatic view of the dual lumen catheter inserted in the subclavian vein of a patient.
Figure 1:
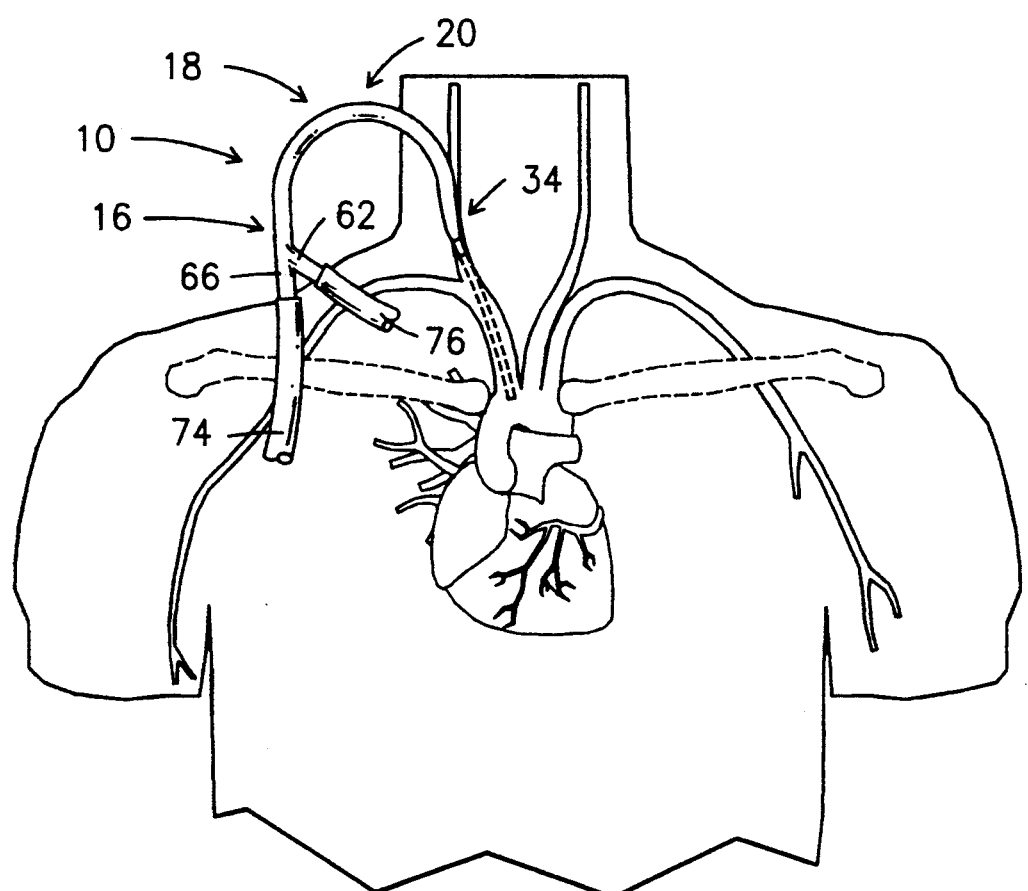
FIG. 1 is a diagrammatic view of the dual lumen catheter inserted in the internal jugular vein of a patient.

As shown in FIGS. 1 and 2, the present invention relates to a dual lumen catheter generally indicated as 10 configured to be operatively coupled between a patient P and a dialysis device (not shown) for hemodialysis treatment or the like.

As best shown in FIG. 2, the dual lumen catheter 10 comprises an outer extraction lumen generally indicated as 12 having an inner return lumen generally indicated as 14 disposed therein. The outer extraction lumen 12 and the inner return lumen 14 are similarly configured to cooperatively form a proximal section generally indicated as 16, an arcuate intermediate section generally indicated as 18 circumscribing an arc of substantially 180 degrees and a distal section generally indicated as 20.

As best shown in FIG. 2, the outer extraction lumen 12 comprises a hollow extraction tube or conduit 22 including a substantially straight proximal extraction portion 24, an arcuate intermediate extraction portion 26 and a substantially straight distal extraction portion generally indicated as 28. The substantially straight distal extraction portion 28 comprises a first extraction region 30 having a first diameter and a second extraction region 32 having a second diameter less than the first diameter of the first extraction region 30 including a reduced tip 34 with an inclined surface or truncated wall 36 on the end thereof disposed in operative communication relative to each other by an extraction transition region 38. A plurality of extraction apertures each indicated as 40 is formed through the wall of the second extraction region 32.

As best shown in FIG. 2, the inner return lumen 14 comprises a hollow return tube or conduit 42 including a substantially straight proximal return portion 44, an arcuate intermediate return portion 46 and a substantially straight distal return portion generally indicated as 48. The substantially straight distal return portion 48 comprises a first return region 50 having a first diameter and a second return region 52 having a second diameter less than the first diameter of the first return region 50 including a reduced tip 54 with an inclined wall 56 on the end thereof disposed in operative communications relative to each other by a return transition region 58. A return aperture 60 is formed in the end of the reduced tip 54.

As best shown in FIG. 2, the proximal section 16 is secured to a Y-shaped hub generally indicated as 61 including an extraction leg 62 having an extraction channel 64 formed therethrough and a return leg 66 having a return channel 68 formed therethrough. The distal end 70 of the Y-shaped hub 61 is coupled to the proximal section 16 of the dual lumen catheter 10; while, the proximal end of the extraction leg 62 and return leg 66 each includes an attachment means 72 to secure a flexible extraction conduit 74 and a flexible return conduit 76 in operative relationship to the outer extraction lumen 12 and inner return lumen 14 respectively. A clamp 78 may be coupled to either the flexible extraction conduit 74 or the flexible return conduit 76 to control the liquid through either flexible conduit 74 or 76.

FIG. 1 shows a dual lumen catheter 10 in the internal jugular vein of a patient P. Since the internal jugular vein runs parallel to the long axis of the body and is entered at the base of the neck dorsal to the clavicle, straight catheters used in this location have to be secured to the side of the neck and usually end up kinking, whereas the arcuate configuration can be secured to the anterior chest wall and thereby resists kinking. Internal jugular catheterization is becoming the preferred method of temporary dialysis since it is not predisposed to stenosis as is the case with subclavian catheterization. However, the arcuate configuration does not limit its use to the internal jugular. In patients with narrow chests or where entry into the subclavian is more lateral than usual the arcuate configuration will permit it to be secured to the anterior chest wall without risk of kinking. The dual lumen catheter 10 may be secured in place by a conventional dressing 80 and attachment fitting having wing tabs, As shown, the dual lumen catheter 10 passes through the dressing 80 and inserted through the skin and into the subclavin vein in the downstream direction. As shown in FIG. 1, the multilumen catheter 10 may comprise a substantially constant cross-section with a reduced tip 34 or a decreasing cross-section in the distal section 20 as shown in FIG. 2.

For use in hemodialysis, the double lumen catheter 10 is introduced in the direction of blood flow in a large vein over a hypodermic needle, Seldinger's guide wire or through a sheath as described in U.S. Pat. No. 5,057,073. The blood is drawn from the patient P through the extraction aperture 40 and outer extraction lumen 12 for processing by the dialysis device (not shown) and is returned through the inner return lumen 14 and return aperture 60.

Although the inner return lumen 14 is described as disposed within the outer extraction lumen 12, the inner return lumen 14 and outer extraction lumen 12 may be disposed in side by side relationship. Moreover, the catheter 10 may comprise three or more lumens.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A multilumen catheter comprising an extraction lumen including a proximal extraction portion and a return lumen including a corresponding proximal return portion coupled to a medical device, an arcuate intermediate section, and a distal section to be partially placed into the patient wherein the cross-sectional area of said extraction lumen and said return lumen in said proximal section is greater than the cross-sectional area of said extraction lumen and said return lumen in at least a portion of said distal section, said distal extraction portion comprises a first extraction region having a first cross-sectional area and a second extraction having a second cross-sectional area less than said first diameter of said first extraction region disposed in spaced relationship relative to each other by an extraction transition region having a proximal end and a distal end wherein the cross-sectional area thereof decreases from said proximal end and to said distal end and said distal return portion comprises a first return region having a first diameter and a second return region having a second diameter less than said first diameter of said first return region diameter disposed in operative communication relative to each other by a return transition region to reduce the creation of fluid pressure resulting from the flow of fluid through said multilumen catheter.

2. The multilumen catheter of claim 1 wherein said second return region is concentrically disposed within said second extraction region.

3. The multilumen catheter of claim 2 wherein said second extraction region includes a reduced tip on the end thereof and said second return region includes a reduced tip on the end thereof.

4. Them multilumen catheter of claim 3 wherein said reduced tip of said second extraction section includes a plurality of extraction apertures formed therethrough and said reduced tip of said second return region includes a return aperture formed therethrough.

5. The multilumen catheter of claim 1 wherein said arcuate intermediate section circumscribes an arc of substantially 180 degrees.

* * * * *